United States Patent [19]

Yakich

[11] Patent Number: 4,549,860

[45] Date of Patent: Oct. 29, 1985

[54] BLOOD PUMP IMPROVEMENTS

[76] Inventor: Sam S. Yakich, 830 S. Saratoga Ave. Apt. C-103, San Jose, Calif. 95129

[21] Appl. No.: 672,815

[22] Filed: Nov. 19, 1984

Related U.S. Application Data

[63] Continuation-in-part of Ser. No. 481,712, Apr. 4, 1983, abandoned.

[51] Int. Cl.⁴ ............................................. F04B 43/12
[52] U.S. Cl. .................................... 417/475; 417/477
[58] Field of Search ................................ 417/474–477

[56] References Cited

U.S. PATENT DOCUMENTS

| 2,789,514 | 4/1957 | Hill | 417/477 |
| 2,831,437 | 4/1958 | Cromwell et al. | 417/477 |
| 3,402,673 | 9/1968 | Ballentine et al. | 417/477 |
| 3,649,138 | 3/1972 | Clay et al. | 417/477 |
| 3,712,762 | 1/1973 | Kenney | 417/477 |
| 3,822,948 | 7/1974 | Handl | 417/477 |
| 4,012,177 | 3/1977 | Yakich | 417/477 |
| 4,214,855 | 7/1980 | Gerritsen | 417/477 |

FOREIGN PATENT DOCUMENTS

WO8204291 12/1982 PCT Int'L Appl. ............... 417/475

Primary Examiner—Leonard E. Smith
Assistant Examiner—Theodore Olds

[57] ABSTRACT

The main application of this pump is for human heart coronary bypass, cardiac and transplant surgery. A non-occlusion blood pump of peristaltic type and blood pump tube element with pulsating pressure pump delivery, giving similar momentum to blood flow as a natural heart beat, needed to penetrate the capilaries, tiny blood vessels of human body. Most important improvement in this pump is in an especially conceived blood pump tube element which reduces hemolysis of blood by first being partially squeezed during pumping and thus not requiring any occlusion adjustments, second by its elements so structured to minimize internal flow friction and turbulance, both of these minimize the hemolysis of blood, as proved by tests. The devices comprised basically of two but not necessarily, blood pump tube elements. These elements are engaged by two sets of rollers driven in a circular path by an electric motor, one set is compressing the tube partially, while the other set is reshaping the tube, one roller at the time, thus reducing stresses on tube wall. This action causes series of discharge and suction pump cycles called pumping. Additionally, the relative position of the rollers to blood pump tube elements may be adjusted to change the delivery rate of blood by the pump. Said delivery change combined with continuous change of RPM (electronically) of an AC motor driving the pump allows this blood pump to deliver at same (or different) rate at wide range of frequencies (number of pulses per min.). This may open a new and exciting possibilities where some of diseases of human body may be treated by selective and optimized blood delivery/frequency applied locally to (detached from its own heart) diseased organ or part of human body, while the heart is active for the rest of the body.

None of the blood pumps presently on the market are able to deliver selectively, at desidered rate and frequency of pulse, the blood to the patient.

1 Claim, 7 Drawing Figures

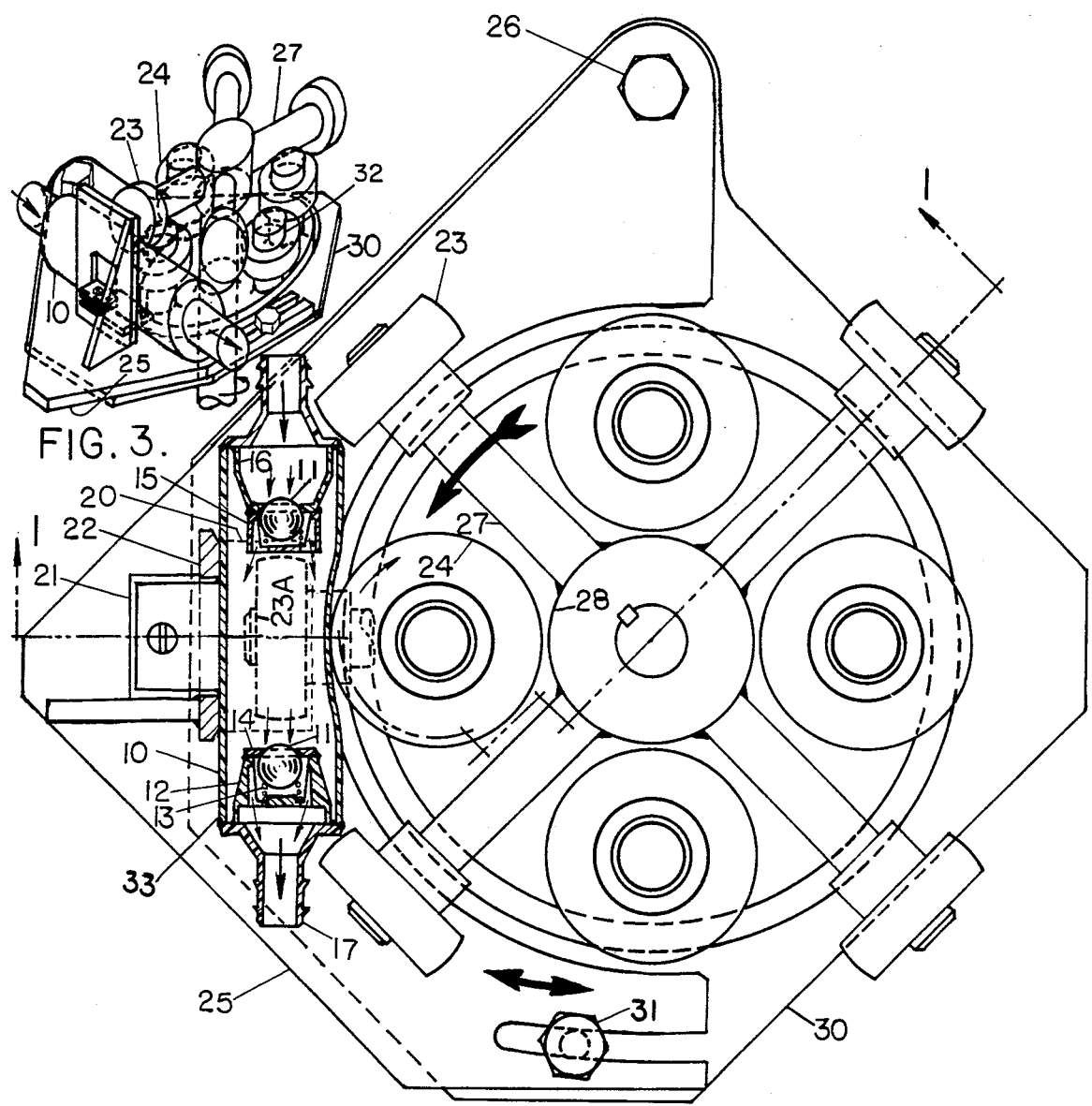
FIG. 3.
FIG. 2.
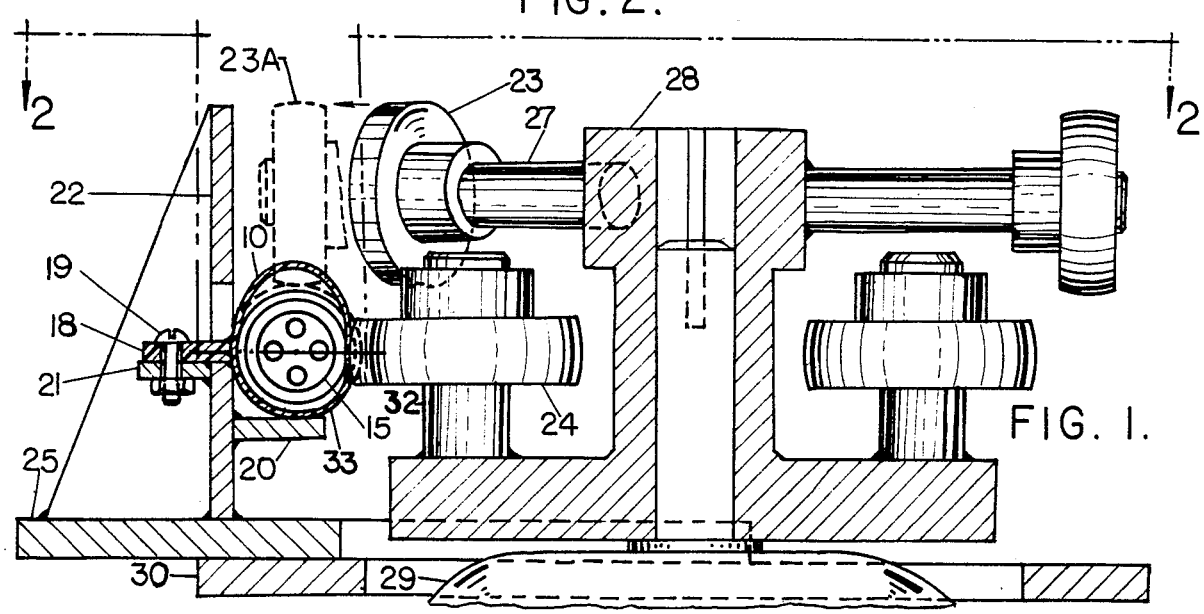
FIG. 1.

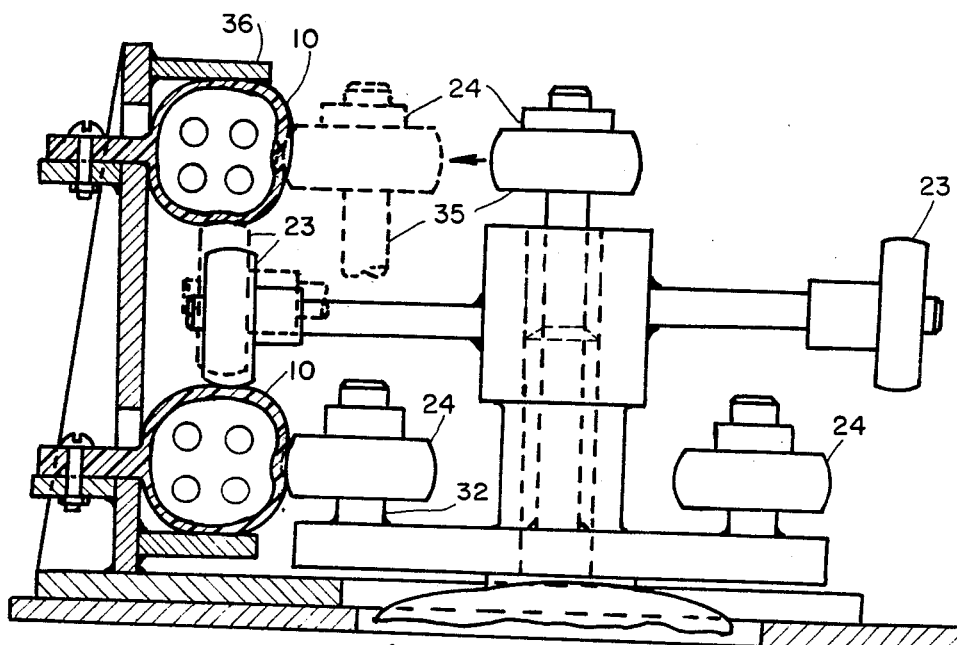
FIG. 4
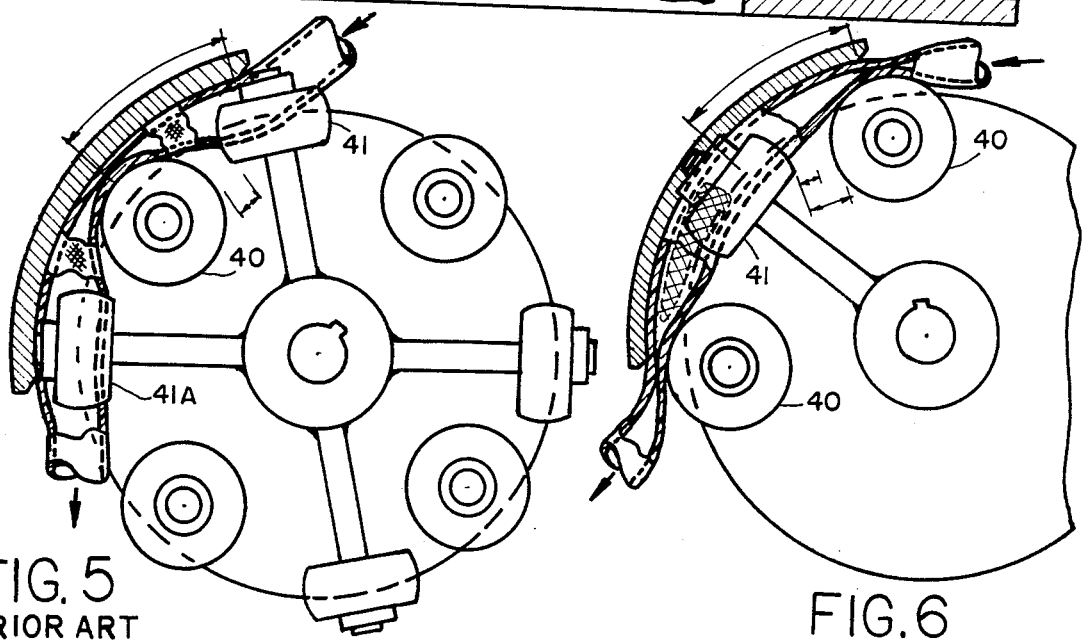
FIG. 5
PRIOR ART
FIG. 6
PRIOR ART
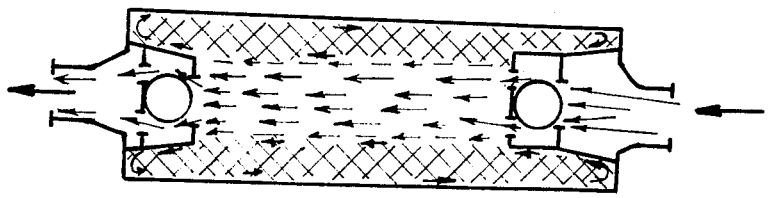
FIG. 7

BLOOD PUMP IMPROVEMENTS

This application is a continuation-in-part of Ser. No. 06/481,712, filed on 4/4/83 and now abandoned.

BACKGROUND OF PRIOR ART AND PROPOSED IMPROVEMENTS

Proposed improvements as depicted in this paper are an effort to make better my own blood pump patented under U.S. Pat. No. 4,012,177, main thrust for improvements here is to get a simpler structure and improve hemolysis, while not changing superior features of ref. #6 pump, namely: partial tube's squeeze by means of employing two check valves to replace rollers valving action, requiring total continuous squeeze over a long and wide path of the tube in order to maintain the delivery of blood at pressures required, namely 720 mmHg or 12.7 PSI. Major problem in conventional blood pumps is that they use the rollers not only to move the fluid, but also to maintain the pressure in discharge part of tubing, to do so all their rollers have to squeeze flat the tubing along the whole length of contact. Large area of blood film is trapped along inside whole surface of tube contact under mechanically adjusted (from outside) pressure by rollers. Blood cells like eritrocites in said film are destroyed and debris of this destruction-free hemoglobine is washed away by each new roll into the blood stream, while fresh blood covers inside tube area again, this causes hemolysis. We will discuss this later in more detail. Simplification of elements was also very important, hard to fabricate, as suggested in U.S. Pat. No. 4,012,177, Blood Pump Tube Element (in brief BPTE) now is conceived to be straight and in such a position relative to rollers to permit only one roller at a time to depress partially the tube wall of BPTE. Tube reshaping rollers were introduced, prior art in themselves, but in combination with partial tube squeeze, this presents first time that reshaping rollers will be successfully used, in view that in prior art tube reshaping from fully flat to circular introduces very high hoop stresses in tube. This stress problem in conventional pumps using tube reshaping rollers will be discussed now in connection with FIGS. 5 & 6. Reduction of stress in tube's wall means more reliable blood pump. Conventional blood pumps place "reshaping" rollers one at the top and one at the bottom of a tube at a distance approximately ⅛" from the tube, one pair in front, one pair behind the tube's compressing roller, and they mainly don't reshape, but they guide the tube. FIG. 5 illustrates a case when reshaping roller #41 is placed too close to compressing roller #40 and at a distance of 0-1/32" from tube, crosshatched areas of tube present locations on a tube where overstress (cracks) will occur. Roller #41A is shown on FIG. 5 to depict together with #41 the location of tube's guide rollers in prior art. FIG. #6 shows that if rollers #40 and #41 are spread more apart it will not help much. Ultimately, by reducing the diameter of rollers or increasing the size of pump, rollers #40 and #41 are so far apart, stress problem will be over, but tube by itself (far away from compressing roller) will recover to circular shape, thus reshaping rollers will become superfluous. Conventional pumps, in view of above limitations, have to depend on elasticity of their tube walls for amount of recovery time, i.e. suction time. More plastic walls—longer time, smaller delivery, so said pumps will not be able to increase the delivery by increasing its RPM after a point where said suction time lags increase in RPM. Proposed pulsating blood pump (in brief PBP) here, with improvements recited above, will increase the delivery with increase in RPM without above limitations. The delivery of PBP may also be effected by depressing tube wall #33 more or less by roller(s) #24. The choices to change delivery two ways allow the trade of, namely, PBP may be set to run at higher RPM and smaller tube displacement to optimize the durability of BPTE, this may look like an obvious choice, but none of the referenced pumps has this feature. Unlimited increase in its RPM of PBP combined with pulsating delivery opens up a new avenue, in some future day, where this type of pump may be used to speed up a cure of some of the human diseases. It is observed that normal reaction of human body to combat some infections: bacterial, viral, by increased pulse rate (temperature) apparently rushing antibodies, leukocytes and others at increased rate (pulse) to fight invaders. Above suggestion may be called highly speculative and in layman's language, but say if only for sake of test supply of blood to diseased area is increased to say 300 pulses per minute by use of outside pump (blood diverted and returned to normal patient stream after a while) would this have a healing effect or would some other rates than 300 ppm or other person's blood or fluid (vaccine) be curvature remains to be answered. No test(s) have been made in this area, but this author suggests that PBP as conceived may be at least used for this kind of research besides its main application for heart coronary bypass and transplant surgeries. Integral part of the improvements of PBP is the hub #28 conceived to be directly mounted on electric motor's output shaft (RPM of this motor may be changed electronically). Many of the conventional blood pumps have (mechanical gears or V-belt) reductors which decrease their reliability and add to cost. All of, or most of, blood pumps have a hand crank which (in case of catastrophic failure of electrical or mechanical parts) is used to run pump by hand. PBP's hub #28 has a ~ twice longer keyway hole in a center than needed for mounting said hub #28 on an electric motor, provided for a hand crank, this obvious safety feature is recited here for purposes of pointing out that conventional pumps with reductors are much harder to move by hand from reduction side because of resistance of the reductor. PBP has a clear advantage in this area. Another ultimate safety feature of PBP is BPTE #10 which alone, out of PBP, may pump the blood by outside operator depressing its tube walls by fingers of his hands. This may be obvious to many, but it is mentioned here to stress the adaptability and functionality of PBP in its simplest form. In this respect BPTE resembles some prior art syphon tubes. However none of prior art syphons would be able to work in the electro-mechanical pump such as PBP without improvements on syphons and pump, needed for blood pumping, as suggested here for PBP. Following future research breakthroughs BPTE #10 alone may be used to prolong (save) the life of heart failure (attack) victims before medics will be able to reach them. In this vision that neighbors and/or relatives may be able to connect the BPTE, say to left hand artery and vein near heart's ventricule/chamber and temporary by hand pump blood say for 10–20 minutes, until the help arrives. This highly speculative suggestion is written in layman's language and may be incorrect from today's medical standpoint, but if nothing else it may trigger a research in this area and at this time. Not to lose contact with reality, it is stressed again that at the present time, main application of PBP is for coronary bypass and heart transplant operations. Said hub has four rollers #24 conceived to compress, and four rollers #23 conceived to reshape tube #33, said rollers are mounted by their respective shafts #27 and #32 to said hub in a simple way, FIGS. 1, 2 and 3. Requirements for dimensional tolerances in this assembly are almost non-existing in comparison with conventional pump's very tight dim. tolerances required to maintain tube occlusion. All eight rollers are set screw attached to eight shafts and their axial position along said shafts (permanent during pump operation) may be changed, although it is conceived that need for this change will not occur often, since preferred change of pump delivery is by changing its RPM. Also limited movement of sliding plate #25, say $\frac{1}{4}$", will not require said axial adjustment of rollers. The sliding plate is an integral part of PBP conceived to carry one or more BPTEs #10, FIGS. 1, 2 and 3. The plate is pivot (#26) mounted to allow sliding and bolted down by screw #31 to base #30 to prevent its movement while pump is running. Here also it is pointed out that sliding plate in itself as well as its assembly with BPTE's base plate #30 and hub #28 require no better tolerances on their fabrication dimensions than say 1/16" plus-minus. Result is the same: This PBP doesn't require occlusion adjustment. FIG. #4 is illustrating an arrangement where two BPTEs #10 are placed above each other. Rollers #23 are staggered in order to touch to reshape only upper or only lower BPTE, one at a time. FIG. #4 shows the structure of reduced to practice PBP, my prototype. FIG. #4 shows two rollers #24 are attached to longer shafts #35 while other two are attached to short shafts #32, also an extra plate #36 is placed on top of upper BPTE, equivalent to plate #20 in FIGS. 1 and 2. Simplicity, loose dim. tolerances and cost are improvements here over the conventional blood pumps.

The most important improvement in my PBP is the structure of BPTE #10. This structure shape of check valves and shape of their body placed inside tube #33 form with said tube two internal cavities to effect formation of relatively stagnant "dead" blood flow zone essential to reduction of flow friction and turbulence and so hemolysis of blood. FIG. #7 illustrates this effect where "dead" flow zone is approximately depicted by crosshatched areas. Main flow in a middle shown by arrows while some of remaining "back flow" and turbulance shown by arrows near the tube's wall. Picture similar to FIG. #7 was observed in tests. Test results (mainly amount of free hemoglobin as a measure of destruction of eritrocites, in blood, by pump action) will be disclosed later. Test is also a measure of friction and turbulence inside the BPTE. Without recited improvements above and construction as shown (FIGS. 1 and 2) of BPTE the PBP will be impossible. Continuous blood flow pumps, widely used at present time, deliver blood at near non-pulsating pressure because rollers assembly turns at constant speed. Some major blood pump manufacturers (indirectly admitting shortcomings of continuous flow pumps) have made so-called "pulsatile pressure" new line of blood pumps at the expense of adding complicated electro-mechanical brakes to their continuous flow blood pumps now in use and marketed. There is no doubt, "pulsatile flow" of blood is made at high cost, namely increase in hemolysis, and as in any complicated device, drop in reliability. Full pulsating blood flow, as achieved with simple device such as PBP, is a major improvement only if it is achieved with comparably low hemolysis of blood effect. Continuous blood pump delivery tends to poorly supply with oxygen periferal (distant from the heart) human body organs. This problem is very much pronounced in the cerebral region, namely starvation in oxygen is causing destruction of brain cells. As explaned here, pulsating flow is very much desirable for good perfusion. The PBP is superior to continuous flow pumps, as mentioned earlier, by ability to generate relatively high pressure pulses, say 720 mm Hg or 12.7 PSI, this needed to penetrate the average oxigenator plus human body if oxigenator is placed at discharge port of PBP. When the oxigenator is placed next to suction port of some conventional pumps, this is a poor choice, since it will be undesirable to pressurize blood vessels in human body to say 720 mm Hg by placing patient in front of oxigenator. The prior art states the reason for this is that pump shall suck from instead of pushing through blood in oxigenator. Some of the large vessels like great aorta $\frac{3}{4}$"–1" in diameter, 0.03"–0.02" thick wall, may see hoop stress 100–150 PSI, which may propagate cracks in walls of large blood vessels, especially in older patients. Imagine if oxigenator gets clogged up and pressure check-up system fails, some of large blood vessels now will burst for sure. Another possibility of clogged up oxigenator (when blood is sucked from it) that vacuum in pump is low (back flow) due to occlusions, so conventional pump becomes unoperable. Advantage here is that PBP shall have as conceived the oxigenator always first connected to discharge, so after loosing 500 mm Hg through oxigenator, next, blood vessels of patient will see only about 200 mm Hg and then blood will go to a return container (placed about 4 feet above suction port of BPTE for priming purposes of pump) and than back to said suction port thus completing the cycle. Raise in 200 mm Hg of about 80 mm Hg is due to said 4 foot elevation of return container which in itself is beneficial for keeping the air out of the system. Due to technical difficulties to connect directly to blood flow differential manometer and then pressure transducer to sense velocity pressure (theoretical method to determine the rate of flow in closed fluid circuits) conventional pump manufacturers would calibrate their digital flow meters by actually measuring the output of pump at number of RPMs at some pressure. Problem—pressure changes. The flow feed-back control will compare RPM of pump with the RPM of preset flow and feed back the difference to slow down or increase the RPM of electric motor of the pump. This method seems to be right if only median pressure resistance by which they calibrated the pump would be close to actual resistance to the flow, the pressure, as seen in part above, may be changing greatly, for example if oxigenator resistance to flow due to clogging goes say from 500 mm Hg to 1000 mm Hg actual rate of flow will fall more than twice because 1000 mm Hg may cause back flow (roller's mechanical pressure against the tube insufficient to keep it shut) but this change in flow will not show on digital meter, so since it will not be noticed, it will not be corrected. Check valves of PBP will have practically no leaks to cause fluid back flow and than when calibrated properly, change in flow alone will not change RPM of pump, instead flow or pressure changes or both will trigger feed back electrical signal to maintain preset flow rate and pressure as displayed on digital meter. It shall be mentioned also that a pressure transducer for PBP is located at tubing outlet from oxigenator and between oxigenator and patient to sense pressure drop through oxigenator and send electrical warning signal to control loops of pump. Control of flow circuits of PBP are precalibrated so that readout on digital flow meter will be proportional not only to RPM of pump but also to pressure signal of said pressure transducer. Blood flow regime now is in true visual and electromechanical control. Conventional pumps, even if they had made all above calibrations may have false blood flow rate readout, and its correction (due to the potential uncontrollable drops of pressure caused by backflow leaks inherent in these pumps caused by unpredictable occlusion) is undependable. Not to lose the sense for major improvement namely less hemolysis in view of above recited improvements, once more we have to dramatize the awesome agitation of blood cells during the average heart coronary bypass surgery, lasting say four hours. Tightly pressing the tube flat, rollers of conventional blood pumps engage said tube (say ½" ID on length of about 12") over 18.8 sq. in. about 192,000 times during four hours time (4 rollers/rev.×200 RPM×240 min.). The word agitation may as well be called *destruction* of blood cells. Long heart transplant operations may reach one million tube engagements. Although there are a number of methods used to test the amount of blood cells destruction during the pumping process like: free hemoglobin count test, hematocrit and heptoglobine tests, etc., full account of real damage to human body, after one of these surgeries, may only be assessed by the length of time that each individual patient takes for a full recovery. It is also estimated that 10–15% more of patients may survive the ordeal of surgery if pumps used were less hemolytical. The PCT reference No. WO 82/04291 discloses a pump that illustrates that prior art.

To be more specific here, test results of my PBP and PCT reference #9 will be reduced here to comparable test conditions. Leading conventional pump, LCP in brief, test results will also be shown.

Test parameters and conditions for my PBP and LCP are: Bovine blood recirculated, return container placed at 3¼' above the pump discharge valve to simulate ~80 mm Hg resistance to flow. LCP pumping against 40 mm Hg column of blood, no oxigenators connected in the flow circuits of either pump. The discharges were set for 4.0 lit/min at 180 RPM, testing time 3.0 hours. The data for PCT reference figure #9 indicates that 50 mm Hg and 180 RPM are representative for his test. See pages 3/5 and figure 6, second curve. It is pointed out that due to lower test pressure resistance, mechanical pressure on the pump's tubes (preventing back flow past roller) was set low also. This will be prorated by linear relation, conservatively, since pump delivery pressure resistance, without fluid back flow, is exponentially proportional to mechanical pressure applied to squeeze the tube. In the following simple calculation the method used for linear prorating will be shown. The test results of LCP and PBP for additional free hemoglobin will be converted to (grams/liter/one passage of blood through pump) to conform to the PCT results. Increase in free hemoglobin for LCP was measured 11.7 mg %, i.e. 11.7 mg/100 ml or 117 mg/lit; total flow: (4.0 lit/min×60.0 min×3.0 hr)=720 lit; total number of turns; (3.0 hr×180 RPM×60. Min)=32, 400 turns; for two rollers squeezing the tube per each turn, as in LCP and PBP, the number of comparative blood passages is 64, 800; now 117×720/64,800×1000=0.0013 (g/lit/passage) for LCP; PBP (at 80 mg Hg) exhibits 14.8 mg % free hemoglobin, i.e. 148 mg/lit; now 148×720/64,800×1000=0.0016 (g/lit/passage). Adjusting LCP 2× upwards because it was working against 2× smaller pressure and reducing PCT by ⅔ for having 3 rotor units per turn, PCT, which reported 0.008 (g/lit/passage) because 0.008/1.5=00533.

Summary of Test Results: Comparing the generated free hemoglobin LCP goes to 0.0026 (g/lit/passage) or 58.1% more hemoglobin than PBP. PCT ref exhibits 0.0053 (g/lit/passage) or 233.3% more free hemoglobin than PBP.

Summary to objections to references: Other prior art references show some similar pump elements but do not disclose compatibility for blood pumping but nevertheless if their concepts were to be used for BP, no gap in tube between internal walls means hemolysis; gap or partial gap means inability to maintain blood delivery pressure 12.7 PSI average, tube totally flatened by depressing roller will crack in short time if tube's reshaping rollers are close behind depressing roller. My ref. #6, although it has useful conceptual innovations like: partial squeeze of tube allowed by check valves, is difficult to fabricate; may be also more hemolytical due to mutiplicity of chambers and may have a limit in upper pump's RPM due to the time lag between recovery to round cross section (by elasticity of dual tube walls) and time that next depressing roller will engage the tube.

In view of many years that innovators and manufacturers had not addressed themselves to the problems of existing blood pumps (hemolysis, manufacturing dimensional tolerances to maintain in the occlusion and maintain needed delivery pressure and flow capacity) creation of PBP in a simple manner with full pulsating (not pulsatile) pressure blood flow to add the momentum to penetrate the capillaries, to mention few of the benefits is significant. My recited improvements were not obvious, otherwise somebody will in all these years have manufactured the blood pumps without above problems. Claims of improvements are ever so more valid since this author had built and successfully tested the blood pump with above suggested improvements.

PBP, BRIEF DESCRIPTION OF DRAWINGS

FIG. 1 is an elevation view of the PBP. This view shows also a partial cross section of some PBP's elements. This partial cross section and view is marked in FIG. 2 by arrows 1—1.

FIG. 2 is a plane view of the PBP. This view shows also a partial cross section of some of PBP's elements. This partial cross section and view is marked in FIG. 1 by arrows 2—2.

FIG. 3 is a pictorial isometric view of the PBP. This picture shows BPTE #10, rollers #23 and #24, arms (shafts) #27 and #32 and PBP's supporting base #30 with BPTE's support #25.

FIG. 4 is an elevation view of vertically expanded PBP to contain two BPTE's. Section and view here is similar to view in FIG. 1, except that two rollers #24 are engaging lower BPTE and two others #24 are engaging the upper BPTE, same are in engaging method the rollers #23, also support #25 has an additional plate #36. Incidentally, the test model (prototype) was built per FIG. 4.

FIG. 5 is a plane view sketch of LCP (prior art) made to illustrate overstressing areas (crosshatched) of tube's wall if rollers #41 are used as tube reshaping means (most of LCPs as mentioned earlier use rollers #41 mainly as guides for tube). Notice dimensionless arc and line marking spacing between rollers #40 and #41 are shorter in FIG. 5 than in FIG. 6.

FIG. 6 is a plane view sketch of LCP made to illustrate the loss of LPC capacity in delivery when rollers #41 are placed away from roller #40 and midway between them (to reduce stress). Crosshatched area of the tube here shows volume not refilled per each passage of rollers. Size of pump in FIG. 6 has to be much larger to clearly show this effect of loss in refill and reduction of stress in tube wall by moving rollers #41.

FIG. 7 is a sketch of section (FIG. 2) of BPTE alone made to illustrate blood flow stream lines inside the BPTE. Congregated arrows in a middle of BPTE depict that main portion of blood flow has no contact with inner tube's walls, crosshatched portions depict "dead" flow zone.

DISCUSSION

PBP with here suggested improvements is conceived mainly to be used in medical applications such as coronary bypass, open heart and heart transplant surgical operations, kidney machines, etc. The PBP may use one BPTE as indicated in FIGS. 1, 2 and 3, usually two BPTE's are mounted as shown in FIG. 4. The main advantage, besides others as recited in specifications above, is that combination of improvements suggested will overcome tube's wall stresses. Use of tube reshaping rollers to return tube #33 from oval (partially squeezed) to circular cross section has resolved the stress problem. In LCP of prior art manufacturers were forced to use softer plastics to overcome stress problems, but had to pay for this choice by sluggish recovery of oval to circular cross section of there tubes, this limits increase of RPM for a pump as a means to increase the pump delivery. Soft tube's plastics have another drawback (besides LCP problems above) namely reshaping rollers don't return soft tube in circular but rather to another oval cross section. This makes loss in LCP capacity. PBP however may use harder plastics (due to partial squeeze) which work very nicely with reshaping rollers due to the fact that hard plastics spring back to their circular tube section partially even before the reshaping roller hits them. The improvement (over ref. #6) was that BPTE is now straight with two check valves, one on each end of said straight tube, this change is significant in such a way that only compressing or reshaping roller, one at the time, engages the tube and none of them rollers over the check valves.

Although, as said before, reshaping roller element is a prior art in itself, if said reshaping roller is used as suggested in prior art to recover totally flatened tube they will cause early cracks in tube. In FIG. 5 where rollers #41 are spaced close around the roller #40 it was said that cracks are imminent (even in a soft tube). FIG. 6 shows roller #41 midway the rollers #40 and if FIG. 6 shows construction large enough (there is a limit here like economy in weight, cost, space) stresses may be reduced but loss in capacity of pump (see brief description of PBP above) is also a problem. The PBP improved invention, including the action of rollers #23 and others improvements mentioned above, all add to the following benefits:

a. Enables PBP to change its delivery to ways, first by moving sliding plate #25 with BPTE #10 toward the rollers #24, thus increasing the amount of depression of tube #33 (10), second, at the same unchanged said tube's depression, increase in PBP delivery is possible by increasing (electronically) the RPM of the motor #29.

b. Enables the manufacturers of PBP to use harder plastic materials for BPTE #10, softer plastics may be tested to find trade off point where PBP will work optimally.

Major advantage still is and stays as depicted in my reference #6, namely the elimination of need to calibrate and maintain the *occlusion*, required in all LCP, by PBP concept of *partial* depression of tube. Occlusion here, in brief means maintenance of 0.003-0.005" gap between inner tube walls, early blood pumps required that perfusionist has to set the pump for this occlusion manually, later makes claim they do occlusions automatically. How difficult this problem is will be discussed later in paragraph d.

The side improvements of PBP will be cited:

a. Two-way delivery change provides vital on-the-spot quick PBP blood volume change. Attachment by one screw #19 of BPTE to sliding plate #25, attachment of #25 in turn to base plate #30 by pivot bolt #26 and bolt #31 makes replacements of BPTE's simple and fast. In case of ultimate emergency the BPTE *alone* may be used as a hand pump operated by finger's depressions of its walls by perfusionist.

b. Rollers #23 and #24 due to length and straight shape of BPTE are never running over the check valves, thus eliminating occasional chance (in ref. #6) to not close or to open inadvertantly the check valves.

c. Flexibility of the concept of this PBP to expand vertically by adding to it more than one BPTE #10 and by using a taller spare sliding plate #25 and longer shafts #33 as depicted in FIG. 4. This will make possible to manufacture a multiple delivery PBP's at similar cost as a single BPTE units.

d. Manufacturers of LCP were forced to fabricate their pumps with very close tolerances on dimensions of parts to be assembled, due to rigid requirements imposed onto them by a phanthom of pump *occlusions* adjustments. Accumulation of dimensional tolerances may cause even more tight squeeze of a pump's tube in totally flattened mode than needed for maintenance of pump's delivery pressure (volume), discussed earlier. In the accumulation of tolerances in dimensions of parts (for example $\frac{1}{2}$" has $\pm 1/32$" tolerance on its wall thickness) in the other limit, these accumulations may change the pressure (volume) of pump's delivery from spot to spot along the rollers path of travel. Next, wear and tear of parts may add to this *occlusion* adjustment problem. All these mean more hemolysis and it is a lasting problem to the manfacturers of continuous delivery pumps or LCP's which is haunting them as well as their users. In contrast, proposed PBP needs: no occlusion adjustments, no close dimensional tolerances on its parts or assembly and PBP is insensitive to wear and tear. All above benefits are possible thanks to the concept of *partial* squeeze of its tube (internal tube's gap is $\frac{1}{2}$" or larger always); thus PBP may be manufactured without any big concern for an accumulation of tolerances. Above in itself allows: a direct mounting of hub #28 on the electric motor #29, off the shelf rollers, more economical price of PBP, longer maintenance intervals and thus higher reliability so dearly required in this field.

FIG. 1 shows an elevation view of the PBP, direction of this view and location of its section is given in FIG. 2 by arrows 1—1. FIG. 2 shows a plane view with a partial cross section of PBP, direction and location of which is given by arrows 2—2 in FIG. 1. Electric motor

29 has the hub #28 mounted on its output shaft. Hub #28 (FIG. 1) has permanently attached to its tubular portion four arms (shafts 27), 90° to each others, said arms are in horizontal plane, each arm at its end carry one roller #23 (so called reshaping roller). Disc portion of said hub has permanently attached four arms #32 in vertical direction (FIG. 1) and spaced 90° to each other and 45° to horizontal arms. Vertical arms carry at the ends one roller #24 each, these are tube depressing rollers. All eight rollers are set screw attached to their arms so that rollers position along the arms may be adjusted to optimally engage tube #10. FIG. 4 shows PBP with two BPTEs #10 mounted vertically above each other. This layout requires staggering of rollers #23 so that two of them (180° apart) would, while reshaping upper tube #10, never touch lower tube #10, and two lower rollers #23 shall never touch the upper tube #10. Here also two rollers #24 (180° apart) shall depress the lower tube #10 and two others shall depress the upper tube #10, later is achieved by two longer, vertical shafts #35. Here tube #10 has to be supported by plate #36 from the top to make its reshaping possible. In FIG. 1 the BPTE #10 is attached by one screw #19 to plate #21 which in turn is welded to plate #22. Plate #20 is placed under the BPTE #10 to support it during the reshaping cycle and it is welded to plate #22 which also in turn is welded to sliding plate #25. Electric motor #29 housing is bolted to base plate #30 (not shown) has two threaded holes; one to accept bolt #26 which pivots sliding plate #25, the other to accept the bolt #31 which locks #25 in preselected pump's volume position. Plastic tab #18 is an integral part of BPTE #10 and it has one hole in its center to match a hole in plate #21. Even the screw #19 is holding tight BPTE #10 through said holes to plate #21, the nature of joint between tab #18 and tube #33 is semiflexible (due to wall flexibility of tube #33) and beneficial to reduction of stresses in tube #33 when either of rollers #23 or #24 initially hits the tube #33. Rollers as assembled are advancing against BPTE #10 in a circular path, in FIG. 1 roller #24 is shown to partially depress the tube #33, while roller #24 now starts to disengage, reshaping roller #23 starts to engage the tube #33, the full reshaped position of tube #10 and position of #23A is shown in phanthom lines.

FIG. 2 shows a section through BPTE #10 in horizontal plane where also roller #24 depresses wall of tube #33.

BPTE #10 shall be fabricated from an elasto-plastic material such as polypropylene or polyethylene. The remaining components of PBP shall be fabricated from metallic materials such as aluminum or stainless steel. The BPTE #10 shall be fabricated by first placing one spherical ball #11 and one helical spring #13 into conical part #12, then ball's seat #14 shall be fused (plastic welded) on part #12, then this assembly shall be in turn welded to nipple #17, this will complete the discharge check valve. Inlet check valve shall be fabricated by first welding ball seat #16 to nipple #17 and then placing one spring #13 and one ball #11 inside seat #15 and welding it to #16. Two check valves then, one on each end, shall be welded to tube #33. In mass quantity all plastic parts shall be fabricated by plastic injection molds and weldings may be replaced by sonic or vibration plastic's joining methods. PBP has one return container placed 2-3 feet above inlet check valve (not shown) to create positive pressure 44-66 mm Hg needed to prime this pump and to refill BPTE #10 with blood free of air bubbles after each discharge. In summary, the PBP pumping process goes as follows, refilled with blood, BPTE #10 is depressed into an oval shape by roller #24 and net volume (difference between circular and oval volume of the tube) opens discharge check valve and builds pressure behind its ball #11 to overcome the resistance to blood flow beyond, same pressure acts to press ball #11 against seat #14 preventing back flow. Now in part by its own elasticity and by action of roller #23, tube oval in shape, is pressed against plate #20 back in circular shape to refill itself with blood. Inlet check valve opens to refill but its ball #11 closes tight any backflow in next discharge cycle. Ball #11 seats in #14 and 16 have in a center one large hole, while #12 and 15 have four smaller holes, each to allow free passage of blood. Rollers #23 and 24 are moved in a circular path and in sequence over BPTE #10, one at the time, completing series of discharge and suction cycles called pulsating pumping.

All BPTE #10 parts, plastic and metallic shall be fabricated from biochemically inert materials, then fully decontaminated and stored in airtight sanitized containers before the use.

I claim:
1. A peristaltic type blood pump (in brief PBP) of a pressure pulsating kind that needs no occlusion adjustments consisting of:
   a prime mover electric motor;
   a PBP sliding plate (in brief SP) carrying one or more PBP tube elements (in brief BPTE), said SP has a base plate (in brief BP) in a shape of a right even sided triangle with a large semicircular hole, center of which is located at midpoint of said triangle's diagonal, one pivot hole of said SP located at one 45° corner and one slotted hole, 15° of arc long, at the other 45° corner, said arc has a center at said pivot hole, said large hole allows said SP to be placed in $\frac{1}{4}''-\frac{3}{4}''$ proximity to the later mentioned rollers, said pivot hole allows the SP to swing in an arc getting it closer or further from the rollers, thus enabling side depressions (pumping) of BPTE walls, said slotted hole has a screw in its slot bolted in PSP, when SP is slided in a desired PBP delivery position, said screw prevents the movement of SP while PBP is working, said BP has welded to itself in a proximity of its 90° corner a vertical bracket (in brief VB), one or more rectangular holes are placed on said VB to accept a tab of BPTE, said rectangular holes are placed above each other and spaced in such a way to allow tube reshaping rollers to pass between two BPTE's and in sequence touch only bottom of upper BPTE and then, next tube reshaping roller, only the top of lower BPTE's tube, said VB has welded to itself four horizontal plates (in brief HP), two HP are welded to the inside face of said VB so that one of the HP supports from under the lower BPTE and second HP supports the upper BPTE from the top, third and fourth HP are welded to the outside face of said VB in level with lower edges of said rectangular holes, each of two outside HPs have one hole to match a hole in said tab of each BPTE, one screw and nut are used to attach to VB each of the BPTEs;
   a PBP supporting plate (in brief PSP) carrying the prime mover electric motor and PBP sliding plate;
   a PBP hub (in brief PH) pressed directly onto the output shaft of said prime mover electric motor, said PH carry four vertical shafts, one end of each shaft is screwed into a horizontal disc (lower part of said PH), disc has four threaded holes 90° apart placed in a circle close to the edge of said disc, upper plain round part of vertical shafts will have four BPTE's compressing rollers slipped onto them and held tight against said shafts by one set screw each, two of said rollers (placed diametrically opposite to each other) will have a vertical shaft longer to allow its roller to engage the upper BPTE, and two others rollers will have shorter shafts to engage the lower BPTE only, the vertical stem (part of PH) has four horizontal threaded holes (in brief HH), HHs will be positioned at 90° to each other around the circumference of said stem and 45° relative to the holes in said disc of PH, also said HHs shall be staggered so that two HHs, diametrically opposite, will be on a higher level, and other two HHs will be on a lower level, thus allowing reshaping rollers to touch one BPTE while passing untouched second BPTE, said HHs will accept four horizontal shafts one end of which will be screwed in HHs, other end of each horizontal shaft will be plain round and have four tube (BPTE) reshaping rollers slipped onto them and held tight by one set screw each;

each said BPTE being plastic and straight in shape and comprising a long cylindrical tube (in brief CT), CT has fused to its ends two check valves (in brief CV), one CV is at the inlet, second CV is at the outlet of CT, most of a body of CVs is placed inside the CT, inlet CV has three body elements (in brief IBE), first IBE is a nipple which has tubular outside connector barbed on its outside cylindrical surface to prevent leaks when outside tubing is slipped onto it, first IBE extends to a hollow tubular part forming a chamber, the chamber extends to a hollow truncated conical part, second IBE starts with short tubular part which is welded to truncated hollow cone extended at its smaller diameter to a round plate with a large hole in a center, to seat a CV's spherical ball (in brief SB) from the inside of second IBE, first IBE's flange has welded to itself a first short tubular part of second IBE thus forming the inlet CV chamber, third IBE starts with its tubular part fused to said round plate and extends to another round plate having from inside a short round hump to lock on its one end the CV's helical spring (in brief CVHS), said another round plate has four holes around its edges placed 90° apart in a circular pattern, said CT (inside wall) and outside walls of 1st, 2nd and 3rd IBEs form an inside cylindrical cavity open at one end, together with similar cavity of outlet CV they form with CT of BPTE a "dead flow" zone significant in reducing BPTE's internal friction and turbulence causing hemolysis to blood passing through BPTE, said outlet CV comprises also of three body elements (OBE in brief), third OBE, the nipple is same as first IBE, second OBE has a short tubular cavity, one end of it is welded to the said nipple's flange the other end extends in thin round plate with four holes and an internal round hump similar to plate's shape of 3rd IBE, except that four holes now are semiblind and extending themselves into conical part of second OBE, this conical part is truncated and with also truncated conical cavity at its end, this end is welded to the first OBE, first OBE is a somewhat thicker round plate with large hole in its center, to seat the SB, said nipple, short tubular part and in part truncated conical cavities form the outlet chamber of outlet CV, said CT has at his midlength point rectangular tab fused to itself, by this tab BPTE is held semiridgidly (due to elasticity of CT walls) relative to PSP, i.e. relative to rollers, this greatly contributes to reduction of stresses in CT and relaibility of BP as a whole, said inlet and outlet CVs in their above described cavities have each one SB and one CVHS, SB is held up against its seat by precompressed CVHS.

* * * * *